US006582908B2

(12) United States Patent
Fodor et al.

(10) Patent No.: US 6,582,908 B2
(45) Date of Patent: *Jun. 24, 2003

(54) OLIGONUCLEOTIDES

(75) Inventors: Stephen P.A. Fodor, Palo Alto, CA (US); Dennis W. Solas, San Francisco, CA (US); William J. Dower, Menlo Park, CA (US); Xiaohua C. Huang, Mountain View, CA (US)

(73) Assignee: Affymetrix, Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/519,090

(22) Filed: Mar. 6, 2000

(65) Prior Publication Data

US 2001/0053519 A1 Dec. 20, 2001

(Under 37 CFR 1.47)

Related U.S. Application Data

(63) Continuation-in-part of application No. 09/056,927, filed on Apr. 8, 1998, now Pat. No. 6,197,506, which is a continuation of application No. 08/670,118, filed on Jun. 25, 1996, now Pat. No. 5,800,992, which is a division of application No. 08/168,904, filed on Dec. 15, 1993, now abandoned, which is a continuation-in-part of application No. 07/624,114, filed on Dec. 6, 1990, now abandoned.

(51) Int. Cl.$^7$ .............................. C12Q 1/68; C12M 1/34; C07H 21/04
(52) U.S. Cl. ........................ 435/6; 435/288.3; 536/24.1
(58) Field of Search ........................ 536/24.1; 435/288, 435/3, 6

(56) References Cited

U.S. PATENT DOCUMENTS

| 5,569,588 A | * | 10/1996 | Ashby et al. |
| 5,700,637 A | * | 12/1997 | Southern ........................ 435/6 |
| 5,795,724 A | * | 8/1998 | Hillman et al. ................. 435/6 |
| 6,344,316 B1 | * | 2/2002 | Lockhart et al. |

* cited by examiner

*Primary Examiner*—Stephanie W. Zitomer
(74) *Attorney, Agent, or Firm*—Morgan, Lewis & Bockius LLP

(57) ABSTRACT

The present invention provides a number of oligonucleotide sequences which can be used for a wide variety of analyses applicable to the diverse fields impacted by the nature of molecular interaction, including chemistry, biology, medicine, and medical diagnostics. In certain embodiments these oligonucleotides may be used as probes to be used in, for example, gene expression analysis.

12 Claims, 5 Drawing Sheets

OLIGONUCLEOTIDES

This application is a continuation in part of U.S. Ser. No. 09/056,927 U.S. Pat. No. 6,197,506 filed Apr, 8, 1998, which is a continuation of U.S. Ser. No. 08/620,118 U.S. Pat. No. 5,800,992 filed Jun. 25, 1996, which is a divisional of U.S. patent application Ser. No. 08/168,904 filed Dec. 15, 1993 (now abandoned) which is a continuation in part of U.S. patent application Ser. No. 07/624,114 filed Dec. 6, 1990 (now abandoned) each of which is incorporated by reference in its entirety for all purposes.

FIELD OF THE INVENTION

The present invention provides nucleic acid sequences useful for analyzing molecular interactions of biological interest. The invention therefore relates to diverse fields impacted by the nature of molecular interaction, including chemistry, biology, medicine, and medical diagnostics.

SUMMARY OF THE INVENTION

The invention provides nucleic acid sequences for a variety of analyses, including, for example, gene expression analysis. For example, in one embodiment the invention comprises 1 or more, 10 or more, $1\times10^3$ or more, $1\times10^6$ or more, or $1\times10^{12}$ or more nucleic acid sequences containing 10 or more nucleotides for a variety of uses, including, but not limited to, as a probe, as a primer for PCR or as a ligand. In a further embodiment, the invention comprises 10 or more, $1\times10^2$ or more, $1\times10^3$ or more, $1\times10^4$ or more, $1\times10^6$ or more, $1\times10^8$ or more, $1\times10^{10}$ or more, $1\times10^{11}$ or more, $1\times10^{12}$ or more, or $1\times10^{14}$ or more, nucleic probes containing 10 or more nucleotides attached to a solid support to form an array. In a further embodiment, the invention comprises the use of the above array to: monitor gene expression levels by hybridization of the array to a DNA library; monitor gene expression levels by hybridization to an mRNA-protein fusion compound; identify polymorphisms; identify biallelic markers; produce genetic maps; analyze genetic variation; comparatively analyze gene expression between different species; analyze gene knock-outs; hybridize tag-labeled compounds; or perform a wide variety of other analyses.

DETAILED DESCRIPTION OF THE INVENTION

I. Definitions

Figure 1:
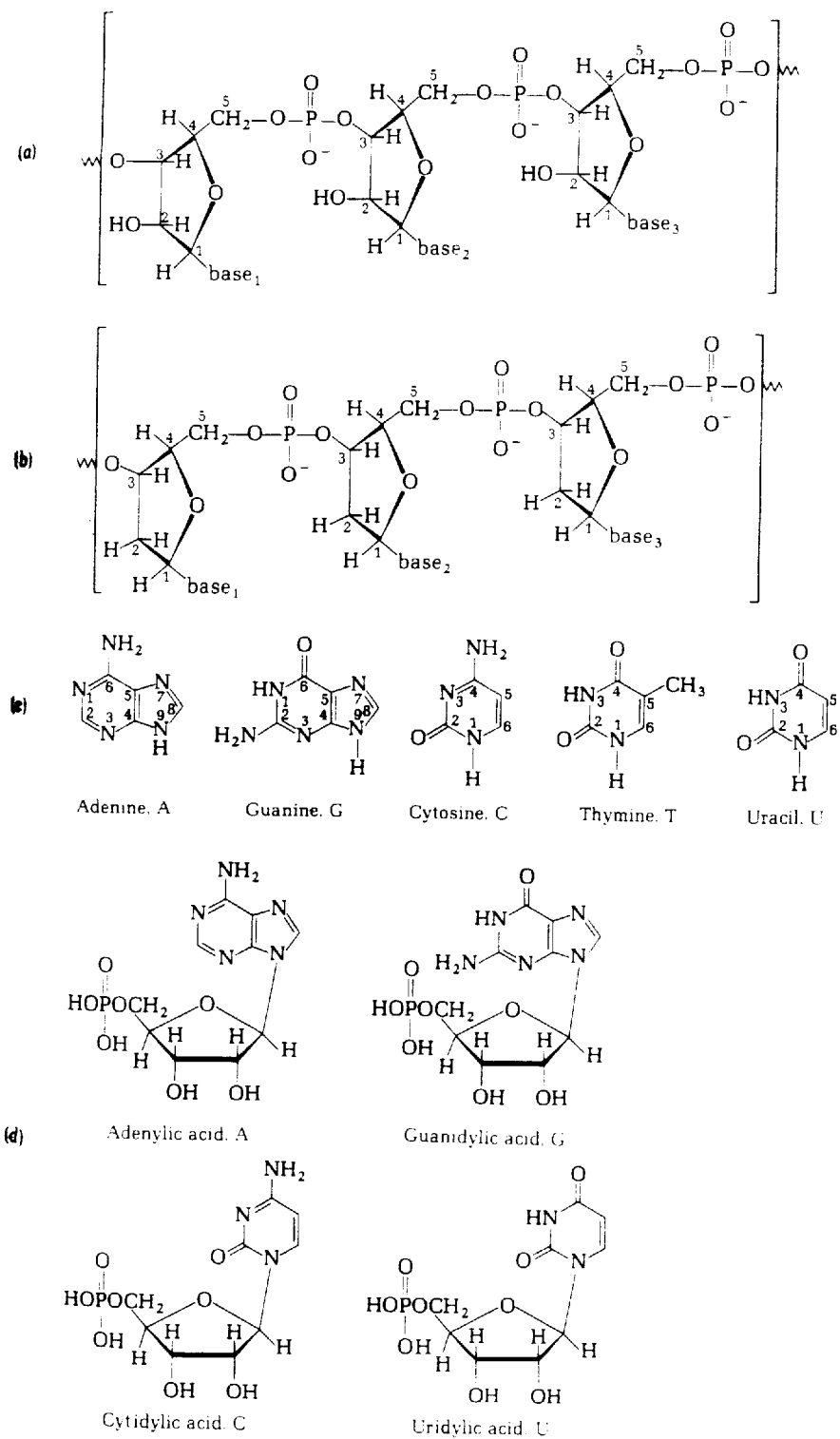
FIGS. 1(a)–1(d) depict the chemical structure of DNA and RNA.

As used herein, certain terms may have the following defined meanings.

As used in the specification and claims, the singular forms "a", "an" and "the" include plural references unless the context clearly dictates otherwise. For example, the term "an array" may include a plurality of arrays unless the context clearly dictates otherwise.

An "array" represents an intentionally created collection of molecules which can be prepared either synthetically or biosynthetically. In particular, the term "array" herein means an intentionally created collection of polynucleotides attached to at least a first surface of at least one solid support wherein the identity of each polynucleotide at a given predefined region is known. The terms "array," "biological chip" and "chip" are used interchangeably.

The array of molecules can be screened for biological activity in a variety of different formats (e.g., libraries of soluble molecules, libraries of compounds tethered to resin beads, fibers, silica chips, or other solid supports). The fabrication of polynucleotide arrays on a solid substrate, and methods of use of the arrays in different assays, are described in U.S. Pat. Nos.: 5,143,854, 5,242,979, 5,252, 743, 5,324,663, 5,384,261, 5,405,783, 5,412,087, 5,424,186, 5,445,934, 5,451,683, 5,482,867, 5,489,678, 5,491,074, 5,510,270, 5,527,681, 5,550,215, 5,571,639, 5,593,839, 5,599,695, 5,624,711, 5,631,734, 5,677,195, 5,744,101, 5,744,305, 5,753,788, 5,770,456, 5,831,070, and 5,856,011, all of which are incorporated by reference herein in their entireties for all purposes. See also, U.S. Ser. No. 09/079, 324, U.S. Pat. No. 6,269,846, and PCT Application WO US99/00730 each of which is incorporated by reference herein in its entirety for all purposes.

"Solid support," "support," and "substrate" refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, fibers or other geometric configurations.

A "discrete, known location" refers to a localized area on a solid support which is, was, or is intended to be used for formation (i.e. placement or fabrication) of a selected molecule and is otherwise referred to herein in the alternative as a "selected" region. The discrete, known location may have any convenient shape, e.g. circular, rectangular, elliptical, wedge-shaped, etc. For the sake of brevity herein, "discrete, known locations" are sometimes referred to as "predefined regions," "regions," or "features." In some embodiments, a discrete, known location and, therefore, the area upon which each distinct compound is synthesized is smaller than about 1 $cm^2$ or even less than 1 $mm^2$. In additional embodiments, a discrete, known location can be achieved by physically separating the regions (i.e., beads, fibers, resins, gels, etc.) into wells, trays, etc.

As used herein, a "polynucleotide" is a sequence of two or more nucleotides. Polynucleotides of the present invention include sequences of deoxyribonucleic acid (DNA) or ribonucleic acid (RNA) which may be isolated from natural sources, recombinantly produced, or artificially synthesized. A further example of a polynucleotide of the present invention may be polyamide polynucleotide (PNA). This invention also encompasses situations in which there is nontraditional base pairing such as Hoogsteen base pairing which has been identified in certain tRNA molecules and postulated to exist in a triple helix. "Polynucleotide" is used interchangeably with "oligonucleotide" is this application.

The terms "nucleotide" and "nucleic acid base" include deoxynucleotides and analogs thereof. These analogs are those molecules having some structural features in common with a naturally occurring nucleotide such that when incorporated into a polynucleotide sequence, they allow hybridization with a complementary polynucleotide in solution. Typically, these analogs may have one or more modified bases, as well as modified forms of ribose and phosphodiester moieties. The changes can be tailor made to stabilize or destabilize hybrid formation, enhance the specificity of hybridization with a complementary polynucleotide sequence as desired, or enhance stability of the polynucleotide.

Analogs also include protected and/or modified monomers as are conventionally used in polynucleotide synthesis. As one of skill in the art is well aware polynucleotide synthesis uses a variety of base-protected nucleoside derivatives in which one or more of the nitrogens of the purine and pyrimidine moiety are protected by groups such as dimethoxytrityl, benzyl, tertbutyl, isobutyl and the like.

For instance, structural groups are optionally added to the ribose or base of a nucleoside for incorporation into a polynucleotide, such as a methyl, propyl or allyl group at the 2'-O position on the ribose, or a fluoro group which substitutes for the 2'-O group, or a bromo group on the ribonucleoside base. 2'-O-methyloligoribonucleotides (2'-O-MeORNs) have a higher affinity for complementary polynucleotides (especially RNA) than their unmodified counterparts. 2'-O-MeORNA phosphoramidite monomers are available commercially, e.g., from Chem Genes Corp. or Glen Research, Inc. Alternatively, deazapurines and deazapyrimidines in which one or more N atoms of the purine or pyrimidine heterocyclic ring are replaced by C atoms can also be used.

The phosphodiester linkage, or "sugar-phosphate backbone" of the polynucleotide can also be substituted or modified, for instance with methyl phosphonates, O-methyl phosphates or phosphorothioates. Another example of a polynucleotide comprising such modified linkages for purposes of this disclosure includes "peptide polynucleotides" in which a polyamide backbone is attached to polynucleotide bases, or modified polynucleotide bases. Peptide polynucleotides which comprise a polyamide backbone and the bases found in naturally occurring nucleotides are commercially available from, e.g., Biosearch, Inc. (Bedford, Mass.). See also U.S. Pat. Nos. 5,773,571 and 5,786,461, each of which is incorporated by reference in its entirety for all purposes.

Nucleotides with modified bases can also be used in this invention. Some examples of base modifications include 2-aminoadenine, 5-methylcytosine, 5-(propyn-1-yl) cytosine, 5-(propyn-1-yl)uracil, 5-bromouracil, 5-bromocytosine, hydroxymethylcytosine, methyluracil, hydroxymethyluracil, and dihydroxypentyluracil which can be incorporated into polynucleotides in order to modify binding affinity for complementary polynucleotides.

Groups can also be linked to various positions on the nucleoside sugar ring or on the purine or pyrimidine rings which may stabilize the duplex by electrostatic interactions with the negatively charged phosphate backbone, or through interactions in the major and minor groves. For example, adenosine and guanosine nucleotides can be substituted at the $N^2$ position with an imidazolyl propyl group, increasing duplex stability. Universal base analogues such as 3-nitropyrrole and 5-nitroindole can also be included. A variety of modified polynucleotides suitable for use in this invention are described in, e.g., "Antisense Research and Application", S. T. Crooke and B. LeBleu (eds.) (CRC Press, 1993) and "Carbohydrate Modifications in Antisense Research" in ACS Symp. Ser. #580, Y. S. Sanghvi and P. D. Cook (eds.) ACS, Washington, D.C. 1994, each of which is incorporated by reference in its entirety for all purposes.

The terms "nucleic acid," "nucleic acid molecule," or "nucleic acid sequence," refer to a deoxyribonucleotide or ribonucleotide polymer in either single-or double-stranded form, and unless otherwise limited, would encompass analogs of natural nucleotides that can function in a similar manner as naturally occurring nucleotides. Nucleic acids may be derived from a variety or sources including, but not limited to, naturally occurring nucleic acids, clones, synthesis in solution or solid phase synthesis.

A "reference" polynucleotide is a polynucleotide whose hybridization pattern to a probe array is to be compared with the hybridization pattern of a target polynucleotide to another identical or substantially identical probe array. The sequence of a reference polynucleotide may be known but it is not essential that the sequence be known.

"Fragments" of a polynucleotide are portions of the polynucleotide that may be of any length. Such fragments may be single-stranded or double-stranded polynucleotides, or may contain both single- and double-stranded portions.

As used herein a "probe" is defined as a nucleic acid capable of binding to a target nucleic acid of complementary sequence through one or more types of chemical bonds, usually through complementary base pairing, usually through hydrogen bond formation. As used herein, a probe may include natural (i.e. A, G, U, C, or T) or modified bases (7-deazaguanosine, inosine, etc.). In addition, the bases in probes may be joined by a linkage other than a phosphodiester bond, so long as it does not interfere with hybridization. Thus, probes may be peptide nucleic acids in which the constituent bases are joined by peptide bonds rather than phosphodiester linkages.

The term "target nucleic acid" or "target sequence" refers to a nucleic acid or nucleic acid sequence which is to be analyzed. A target can be a nucleic acid to which a probe will hybridize. The probe may or may not be specifically designed to hybridize to the target. It is either the presence or absence of the target nucleic acid that is to be detected, or the amount of the target nucleic acid that is to be quantified. The term target nucleic acid may refer to the specific subsequence of a larger nucleic acid to which the probe is directed or to the overall sequence (e.g., gene or mRNA) whose expression level it is desired to detect. The difference in usage will be apparent from context.

The term "hybridization" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybrids can contain two DNA strands, two RNA strands, or one DNA and one RNA strand.

Methods for conducting polynucleotide hybridization assays have been well developed in the art. Hybridization assay procedures and conditions will vary depending on the application and are selected in accordance with the general binding methods known including those referred to in: Molecular Cloning, A Laboratory Manual, Second Ed., J. Sambrook, et al., Eds., Cold Spring Harbor Laboratory Press, 1989 ("Sambrook et al."); Berger and Kimmel, "Methods in Enzymology," Vol. 152, "Guide to Molecular Cloning Techniques", Academic Press, Inc., San Diego, Calif., 1987; Young and Davis, *Proc. Natl. Acad. Sci., U.S.A.*, 80:1194 (1983), each of which are incorporated herein by reference.

It is appreciated that the ability of two single stranded polynucleotides to hybridize will depend upon factors such as their degree of complementarity as well as the stringency of the hybridization reaction conditions.

As used herein, "stringency" refers to the conditions of a hybridization reaction that influence the degree to which polynucleotides hybridize. Stringent conditions can be selected that allow polynucleotide duplexes to be distinguished based on their degree of mismatch. High stringency is correlated with a lower probability for the formation of a duplex containing mismatched bases. Thus, the higher the stringency, the greater the probability that two single-stranded polynucleotides, capable of forming a mismatched duplex, will remain single-stranded. Conversely, at lower stringency, the probability of formation of a mismatched duplex is increased.

The term "ligation" refers to the process of covalently linking two terminal nucleotides that are on two separate polynucleotide strands, whereby the two strands are joined into one single strand. In the present methodology, in some aspects, hybridization and ligation are accomplished in one step.

An "n-mer" is a single-stranded polynucleotide of "n" number of nucleotides. A "complete set" of n-mers refers to a set of single-stranded polynucleotides of "n" number of nucleotides wherein the set represents every possible combination of the "n" nucleotides. For example, when "n" is 8, a complete 8-mer set contains $4^8$ unique single-stranded polynucleotides. A "substantially complete set" of n-mers represents a set that may not have every possible combination of the "n" nucleotides but provides sufficient number of such single strands to be used as probes such that a target polynucleotide can be characterized. Thus, in some aspects, such a substantially complete set may contain a subset of the single-stranded polynucleotide probes.

The term "substantially identical" as used in the context of array description refers to arrays that may not be identical with respect to each probe composition. For example, two arrays may be substantially identical if one array provides a probe with a certain base at a certain location and the other array provides an analog of that base at the corresponding location.

The term "base call" refers to the determination of the identity of an unknown base in a target polynucleotide. Base-calling is made by comparing the degree of hybridization between the target polynucleotide and a probe polynucleotide with the degree of hybridization between a reference polynucleotide and the probe polynucleotide. In a given case a base call can be made or withheld by selecting a threshold degree of hybridization.

"Mutation" is a change in the nucleotide sequence of a polynucleotide from that of the normal ("wild-type") population. A "substitution" mutation is one in which a nucleotide is replaced by another nucleotide. A "deletion" mutation is one in which one or more nucleotides are deleted from the normal sequence, and an "insertion" mutation is one in which one or more nucleotides are inserted into the normal sequence. A "homozygous" mutation is one that appears in both chromosomes in a diploid organism. A "heterozygous" mutation is one that appears in only one chromosome in a diploid organism, the other chromosome being normal. A mutation can be characterized as, for example, an A→G substitution at position 435.

The phrase "massively parallel screening" refers to the simultaneous screening of at least about 100, preferably about 1000, more preferably about 10,000 and more preferably about 100,000 different nucleic acid hybridizations.

The term "mRNA" refers to transcripts of a gene. Transcripts are RNA including, for example, mature messenger RNA ready for translation, products of various stages of transcript processing. Transcript processing may include splicing, editing and degradation.

"Subsequence" refers to a sequence of nucleic acids that comprise a part of a longer sequence of nucleic acids.

The term "gene knockout, as defined in Lodish et al *Molecular Cell Biology* $3^{rd}$ *Edition,* Scientific American Books pub., which is hereby incorporated in its entirety for all purposes is, is a technique for selectively inactivating a gene by replacing it with a mutant allele in an otherwise normal organism.

As used herein the term "genomic library" or "genomic DNA library" refers to a collection of cloned DNA molecules consisting of fragments of the entire genome (genomic library) or of DNA copies of all the mRNA produced by a cell type (cDNA library) inserted into a suitable cloning vector.

"Polymorphism" refers to the occurrence of two or more genetically determined alternative sequences or alleles in a population. A polymorphic marker or site is the locus at which divergence occurs. Preferred markers have at least two alleles, each occurring at a frequency of greater than 1%, and more preferably greater than 10% or 20% of the selected population. A polymorphic locus may be as small as one base pair. Polymorphic markers include restriction fragment length polymorphisms, variable number or tandem repeats (VNTR's), hypervariable regions, minisatellites, dinucleotide repeats, trinucleotide repeats, tetranucleotide repeats, simple sequence repeats, and insertion elements such as ALU. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic or biallelic polymorphism has two forms. A triallelic polymorphism has three forms.

A "genetic map" is a map which presents the order of specific sequences on a chromosome.

A "genetic variation" refers to variation in the sequence of the same region between two or more organisms.

An "mRNA-protein fusion" is a compound whereby an mRNA is directly attached to the peptide or protein it incodes by a stable covalent linkage.

A "ligand" is any molecule, other than an enzyme substrate, that binds tightly and specifically to a macromolecule, for example, a protein, forming a macromolecule-ligand complex. An antisense compound is a ligand which is used to bind a macromolecule for the express purpose of preventing the macromolecule from binding to any other ligand.

Throughout this disclosure, various aspects of this invention are presented in a range format. It should be understood that the description in range format is merely for convenience and brevity and should not be construed as an inflexible limitation on the scope of the invention.

Accordingly, the description of a range should be considered to have specifically disclosed all the possible subranges as well as individual numerical values within that range. For example, the description of a range such as 4 to 50 should be considered to have specifically disclosed all subranges such as 4 to 10, 4 to 20, 4 to 30, 4 to 40, 4 to 50, 5 to 10, 5 to 20 etc., as well as individual numbers within that range, for example, 6, 8, 15, 20, 32, 39, 43, 48 etc. This applies regardless of the breadth of the range. Likewise, a description of a range such as 1 or more, 10 or more, $10^3$ or more, $10^6$ or more, or $10^{12}$ or more should be considered to have specifically disclosed individual numbers within that range as well as higher numbers, for example, 20, $2\times10^4$, $3\times10^8$, $4\times10^{15}$, $5\times10^{18}$, etc.

II. General

The present invention provides nucleotide sequences which alone, or in combinations of 1 or more, 10 or more, $1\times10^3$ or more, $1\times10^6$ or more, or $1\times10^{12}$ or more, can be used for a variety of applications.

In one embodiment, the present invention provides nucleotide sequences which are capable of acting as probes, PCR primers, or ligands suitable for a variety of applications. U.S. Pat. No. 6,020,475 (hereby incorporated by reference in its entirety for all purposes) describes various uses for oligonucleotides and their analogs. The '475 patent states, in part:

Oligonucleotides and their analogs have been developed and used in molecular biology in a variety of procedures as probes, primers, linkers, adapters, and gene fragments. Modifications to oligonucleotides used in these procedures include labeling with nonisotopic labels, e.g. fluorescein, biotin, digoxigenin, alkaline phosphatase, or other reporter molecules. Other modifications have been made to the ribose phosphate backbone to increase the nuclease stability of the resulting analog. Examples of such modifications include incorporation of methyl phosphonate, phosphorothioate, or phosphorodithioate linkages, and 2'-O-methyl ribose sugar units. Further modifications include those made to modulate uptake and cellular distribution. With the success of these compounds for both diagnostic and therapeutic uses, there exists an ongoing demand for improved oligonucleotides and their analogs.

It is well known that most of the bodily states in multi-cellular organisms, including most disease states, are effected by proteins. Such proteins, either acting directly or through their enzymatic or other functions, contribute in major proportion to many diseases and regulatory functions in animals and man. For disease states, classical therapeutics has generally focused upon interactions with such proteins in efforts to moderate their disease-causing or disease-potentiating functions. In newer therapeutic approaches, modulation of the actual production of such proteins is desired. By interfering with the production of proteins, the maximum therapeutic effect may be obtained with minimal side effects. It is therefore a general object of such therapeutic approaches to interfere with or otherwise modulate gene expression, which would lead to undesired protein formation.

One method for inhibiting specific gene expression is with the use of oligonucleotides, especially oligonucleotides which are complementary to a specific target messenger RNA (mRNA) sequence. Several oligonucleotides are currently undergoing clinical trials for such use. Phosphorothioate oligonucleotides are presently being used as such antisense agents in human clinical trials for various disease states, including use as antiviral agents.

Transcription factors interact with double-stranded DNA during regulation of transcription. Oligonucleotides can serve as competitive inhibitors of transcription factors to modulate their action. Several recent reports describe such interactions (see Bielinska, A., et. al., Science, 1990, 250, 997–1000; and Wu, H., et. al., Gene, 1990, 89, 203–209, each of which is hereby incorporated by reference in its entirety for all purposes).

In addition to such use as both indirect and direct regulators of proteins, oligonucleotides and their analogs also have found use in diagnostic tests. Such diagnostic tests can be performed using biological fluids, tissues, intact cells or isolated cellular components. As with gene expression inhibition, diagnostic applications utilize the ability of oligonucleotides and their analogs to hybridize with a complementary strand of nucleic acid. Hybridization is the sequence specific hydrogen bonding of oligomeric compounds via Watson-Crick and/or Hoogsteen base pairs to RNA or DNA. The bases of such base pairs are said to be complementary to one another.

Oligonucleotides and their analogs are also widely used as research reagents. They are useful for understanding the function of many other biological molecules as well as in the preparation of other biological molecules. For example, the use of oligonucleotides and their analogs as primers in PCR reactions has given rise to an expanding commercial industry. PCR has become a mainstay of commercial and research laboratories, and applications of PCR have multiplied. For example, PCR technology now finds use in the fields of forensics, paleontology, evolutionary studies and genetic counseling. Commercialization has led to the development of kits which assist non-molecular biology-trained personnel in applying PCR. Oligonucleotides and their analogs, both natural and synthetic, are employed as primers in such PCR technology.

Oligonucleotides and their analogs are also used in other laboratory procedures. Several of these uses are described in common laboratory manuals such as Molecular Cloning, A Laboratory Manual, Second Ed., J. Sambrook, et al., Eds., Cold Spring Harbor Laboratory Press, 1989; and Current Protocols In Molecular Biology, F. M. Ausubel, et al., Eds., Current Publications, 1993. Such uses include as synthetic oligonucleotide probes, in screening expression libraries with antibodies and oligomeric compounds, DNA sequencing, in vitro amplification of DNA by the polymerase chain reaction, and in site-directed mutagenesis of cloned DNA. See Book 2 of Molecular Cloning, A Laboratory Manual, supra. See also "DNA-protein interactions and The Polymerase Chain Reaction" in Vol. 2 of Current Protocols In Molecular Biology, supra.

Oligonucleotides and their analogs can be synthesized to have customized properties that can be tailored for desired uses. Thus a number of chemical modifications have been introduced into oligomeric compounds to increase their usefulness in diagnostics, as research reagents and as therapeutic entities. Such modifications include those designed to increase binding to a target strand (i.e. increase their melting temperatures, Tm), to assist in identification of the oligonucleotide or an oligonucleotide-target complex, to increase cell penetration, to stabilize against nucleases and other enzymes that degrade or interfere with the structure or activity of the oligonucleotides and their analogs, to provide a mode of disruption (terminating event) once sequence-specifically bound to a target, and to improve the pharmacokinetic properties of the oligonucleotide.

A nucleic acid sequence is made up of four nucleic acid bases attached to a backbone. FIG. 1 shows the structure of two types of nucleic acid sequences: DNA and RNA. 1(a) shows the structure of RNA. 1(b) shows the structure of DNA. 1(c) shows the individual nucleoside bases. 1(d) shows nucleotides (bases attached to backbone structure). Generally, DNA if formed from a backbone comprised of 2'-deoxyribose subunits joined to one of four possible heterocyclic nitrogen containing bases: adenine, guanine, cytosine or thymidine. Generally, RNA is formed from a backbone of ribose subunits joined to one of four possible hetercyclic nitrogen containing bases: adenine, guanine, cytosine or uracil (instead of theymidine.) In some instances, nucleic acid sequences may incorporate one or more, two or more, ten or more or one hundred or more base analogs.

Methods of obtaining nucleic acid sequences of a given length and known sequence and are known to those of skill in the art. Methods of solid phase oligonucleotide synthesis are described in, for example: Advances in the Synthesis of Oligonucleotides by the Phosphoramidite Approach, Beaucage, S. L.; Iyer, R. P., Tetrahedron, 1992, 48, 2223–2311; U.S. Pat. Nos. 4,58,066; 4,500,707; 5,132,418; 4,973,679; 4,415,732; Re. 34,069; 5,026,838. Other methods of obtaining a nucleotide sequence of a given length and known sequence are well known and include various types of molecular manipulation including, but not limited to, enzymatic reactions such as a restriction digestion, ligation, and biosynthesis or methods of amplification of specific regions of nucleic acid sequence such as PCR or LCR. See, Sambrook et al. and Gait (1984) *Oligonucleotide Synthesis: A Practical Approach,* IRL Press, Oxford.

Methods of forming high density arrays of oligonucleotides, peptides and other polymer sequences with a minimal number of synthetic steps are known. The oligonucleotide analogue array can be synthesized on a solid substrate by a variety of methods, including, but not limited to, light-directed chemical coupling and mechanically directed coupling. See Pirrung et al., U.S. Pat. No. 5,143,854 (see also PCT Application No. WO 90/15070) and Fodor et al., PCT Publication Nos. WO 92/10092 and WO 93/09668 and U.S. Pat. No. 5,677,195, which disclose methods of forming vast arrays of peptides, oligonucleotides and other molecules using, for example, light-directed synthesis techniques. See also, Fodor et al., *Science,* 251, 767–77 (1991). These procedures for synthesis of polymer arrays are now referred to as VLSIPS™ procedures. Using the VLSIPS™ approach, one heterogeneous array of polymers is converted, through simultaneous coupling at a number of reaction sites, into a different heterogeneous array. See, U.S. Pat. Nos. 5,384,261 and 5,677,195.

In a further embodiment, the present invention provides nucleotide sequences which when attached to a solid support to form a high density probe array are suitable for a wide variety of array based applications, including, for example, massive parallel gene expression.

Methods of forming high density arrays of oligonucleotides, peptides and other polymer sequences with a minimal number of synthetic steps are known. The oligonucleotide analogue array can be synthesized on a solid substrate by a variety of methods, including, but not limited to, light-directed chemical coupling and mechanically directed coupling. See Pirrung et al., U.S. Pat. No. 5,143,854 (see also PCT Application No. WO 90/15070) and Fodor et al., PCT Publication Nos. WO 92/10092 and WO 93/09668 and U.S. Ser. No. 07/980,523, which disclose methods of forming vast arrays of peptides, oligonucleotides and other molecules using, for example, light-directed synthesis techniques. See also, Fodor et al., *Science,* 251, 767–77 (1991). These procedures for synthesis of polymer arrays are now referred to as VLSIPS™ procedures. Using the VLSIPS™ approach, one heterogeneous array of polymers is converted, through simultaneous coupling at a number of reaction sites, into a different heterogeneous array. See, U.S. application Ser. Nos. 07/796,243 and 07/980,523.

The development of VLSIPS™ technology as described in the above-noted U.S. Pat. No. 5,143,854 and PCT patent publication Nos. WO 90/15070 and 92/10092, is considered pioneering technology in the fields of combinatorial synthesis and screening of combinatorial libraries. More recently, patent application Ser. No. 08/082,937, filed Jun. 25, 1993, describes methods for making arrays of oligonucleotide probes that can be used to check or determine a partial or complete sequence of a target nucleic acid and to detect the presence of a nucleic acid containing a specific oligonucleotide sequence.

In brief, the light-directed combinatorial synthesis of oligonucleotide arrays on a glass surface proceeds using automated phosphoramidite chemistry and chip masking techniques. In one specific implementation, a glass surface is derivatized with a silane reagent containing a functional group, e.g., a hydroxyl or amine group blocked by a photolabile protecting group. Photolysis through a photolithographic mask is used selectively to expose functional groups which are then ready to react with incoming 5'-photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface. Combinatorial synthesis of different oligonucleotide analogues at different locations on the array is determined by the pattern of illumination during synthesis and the order of addition of coupling reagents.

In the event that an oligonucleotide analogue with a polyamide backbone is used in the VLSIPS™ procedure, it is generally inappropriate to use phosphoramidite chemistry to perform the synthetic steps, since the monomers do not attach to one another via a phosphate linkage. Instead, peptide synthetic methods are substituted. See, e.g., Pirrung et al. U.S. Pat. No. 5,143,854.

Peptide nucleic acids are commercially available from, e.g., Biosearch, Inc. (Bedford, Mass.) which comprise a polyamide backbone and the bases found in naturally occurring nucleosides. Peptide nucleic acids are capable of binding to nucleic acids with high specificity, and are considered "oligonucleotide analogues" for purposes of this disclosure.

Additional methods which can be used to generate an array of oligonucleotides on a single substrate are described in co-pending U.S. Pat. Nos. 5,677,195, filed Nov. 20, 1992, and 5,384,261, filed Nov. 22, 1991 and in PCT Publication No. WO 93/09668. In the methods disclosed in these applications, reagents are delivered to the substrate by either (1) flowing within a channel defined on predefined regions or (2) "spotting" on predefined regions or (3) through the use of photoresist. However, other approaches, as well as combinations of spotting and flowing, can be employed. In each instance, certain activated regions of the substrate are mechanically separated from other regions when the monomer solutions are delivered to the various reaction sites.

A typical "flow channel" method applied to the compounds and libraries of the present invention can generally be described as follows. Diverse polymer sequences are synthesized at selected regions of a substrate or solid support by forming flow channels on a surface of the substrate through which appropriate reagents flow or in which appropriate reagents are placed. For example, assume a monomer "A" is to be bound to the substrate in a first group of selected regions. If necessary, all or part of the surface of the substrate in all or a part of the selected regions is activated for binding by, for example, flowing appropriate reagents through all or some of the channels, or by washing the entire substrate with appropriate reagents. After placement of a channel block on the surface of the substrate, a reagent having the monomer A flows through or is placed in all or some of the channel(s). The channels provide fluid contact to the first selected regions, thereby binding the monomer A on the substrate directly or indirectly (via a spacer) in the first selected regions.

Thereafter, a monomer "B" is coupled to second selected regions, some of which can be included among the first selected regions. The second selected regions will be in fluid contact with a second flow channel(s) through translation, rotation, or replacement of the channel block on the surface of the substrate; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form a vast array of sequences of desired length at known locations on the substrate.

After the substrate is activated, monomer A can be flowed through some of the channels, monomer B can be flowed through other channels, a monomer C can be flowed through still other channels, etc. In this manner, many or all of the reaction regions are reacted with a monomer before the channel block must be moved or the substrate must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the substrate. For example, according to some embodiments, a protective coating such as a hydrophilic or hydrophobic coating (depending upon the nature of the solvent) is utilized over portions of the substrate to be protected, sometimes in combination with materials that facilitate wetting by the reactant solution in other regions. In this manner, the flowing solutions are further prevented from passing outside of their designated flow paths.

High density nucleic acid arrays can be fabricated by depositing presynthesized or natural nucleic acids in predetermined positions. Synthesized or natural nucleic acids are deposited on specific locations of a substrate by light directed targeting and oligonucleotide directed targeting. Nucleic acids can also be directed to specific locations in much the same manner as the flow channel methods. For example, a nucleic acid A can be delivered to and coupled with a first group of reaction regions which have been appropriately activated. Thereafter, a nucleic acid B can be delivered to and reacted with a second group of activated reaction regions. Nucleic acids are deposited in selected regions. Another embodiment uses a dispenser that moves from region to region to deposit nucleic acids in specific spots. Typical dispensers include a micropipette or capillary pin to deliver nucleic acid to the substrate and a robotic system to control the position of the micropipette with respect to the substrate. In other embodiments, the dispenser includes a series of tubes, a manifold, an array of pipettes or capillary pins, or the like so that various reagents can be delivered to the reaction regions simultaneously. system to control the position of the micropipette with respect to the substrate. In other embodiments, the dispenser includes a series of tubes, a manifold, an array of pipettes or capillary pins, or the like so that various reagents can be delivered to the reaction regions simultaneously.

U.S. Pat. No. 6,022,714 describes a number of methods for covalent attachment of a polynucleotide to a solid support. In part, the '714 patent states:

A general approach for covalent attachment of a polynucleotide to an insoluble matrix or solid support involves attachment directly to the activated matrix or support without the intervention of a adapter molecule or extensor arm. For example, DNA has been directly attached to cyanogen bromide (CNBr) activated matrices such as agarose. (Arndt-Jovin, D. J., Jovin, T. M., Bahr, W., Frischauf, A-M. and Marquardt, M. Eur. J. Biochem. (1975) 54, 411–418.). DNA has also been directly coupled with CNBr-activated Sephadex. (Siddell, S. G., Eur. J. Biochem. (1978) 92, 621–629.) Another example of direct coupling of DNA to activated cellulose is provided by Biagioni et al. These workers have attached DNA to dichlorotriazinyl cellulose, most likely through the amino groups of adenine, guanine and cytosine (Biagioni, S., Sisto, R., Ferraro, A., Caiafa, P. and Turano, C., Anal. Biochem. (1978) 89, 616–619.).

In addition to direct covalent linkage, a variety of methods have been reported for the indirect covalent attachment of a polynucleotide to a matrix or support by means of a bifunctional molecule first attached to the matrix or activated support. Noyes et al. report the indirect coupling of DNA to cellulose which has been diazotized. The resultant diazotized aryl amine of the cellulose reacts primarily with guanine and uracil (thymine) residues of single strands (Noyes, B. E., and Stark, G. R., Cell (1975) 5, 301–310.). See also Seed, B., Nucleic Acid Res. (1982) 10, 1799–1810. Another example of indirect, covalent attachment involves immobilization of polynucleotides to bisoxirane activated insoluble polysaccharides (Potuzak, H. and Dean, P. D. G., Nucleic Acids Res. (1978) 5, 297–303).

Alternatively, a polynucleotide may first be modified by a bifunctional molecule and subsequently attached to an insoluble matrix or solid support. For example, Dickerman et al. report derivatization of single-stranded DNA with 4-diazobenzoic acid and subsequent covalent attachment of the derivatized DNA to aminopentane Sepharose CL-4B (Dickerman, H. W., Ryan, T. J., Bass, A. I. and Chatteijee, N. K., Arch. Biochem. Biophys. (1978) 186, 218–234.). MacDougall, A. J., Brown, J. G., and Plumbridge, T. W., Biochem. J. (1980) 191, 855–858, describe the alkylation of double-stranded DNA with 4-bis (2-chloroethyl) amino-L-phenylalanine and immobilization of the resultant product of an insoluble support via the primary amino group of the phenylalanine moiety.

Gilham has described direct attachment of polynucleotides to cellulose by a method involving specific activation of the terminal monosubstituted phosphate or polyphosphate of the polynucleotide by a water soluble carbodiimide. (Gilham, P. T., Biochemistry (1968) 7, 2809–2813.).

Chu et al. have described a potentially simple method for attaching amines to the terminal 5'-phosphate of synthetic polynucleotides (Chu, B. C. Wahl, G. M. and Orgel, L. E., Nucleic Acids Res. (1983) 11, 6513–6529.).

Van Boom et al. and Miyoshi et al. have described another immobilization chemistry for tethering 5'-spacer arm synthetic DNA. (Clerici, L., Campagnari, F., deRooij, J. F. M. and van Boom, J. H., Nucleic Acids Res. (1979) 6, 247–258; de Rooij, J. F. M., Wille-Hazeleger, G., Vink, A. B. J., and van Boom, J. H., Tetrahedron (1979) 35, 2913–2926; and (Miyoshi, K., Fuwa, T., European Patent Application, 0101985A1.). In this approach, synthetic DNA with an aliphatic amine spacer arm is reacted with a cyanogen bromide activated support, cellulose or agarose, and is reported to afford attachment only through the spacer arm's amine group.

Array based methods for monitoring gene expression are disclosed and discussed in detail in U.S. Pat. No. 5,800,992, and 6,309,822 and PCT Application WO 92/10588 (published on Jun. 25, 1992), each of which is incorporated herein by reference for all purposes. Generally those methods of monitoring gene expression involve (1) providing a pool of target nucleic acids comprising RNA transcript(s) of one or more target gene(s), or nucleic acids derived from the RNA transcript(s); (2) hybridizing the nucleic acid sample to a high density array of probes and (3) detecting the hybridized nucleic acids and calculating a relative expression (transcription, RNA processing or degradation) level.

The development of light directed synthesis methods such as Very Large Scale Immobilized Polymer Synthesis or VLSIPS™ technology has provided methods for making very large arrays of nucleic acid probes on very small substrates. See U.S. Pat. No. 5,143,854 and PCT patent publication Nos. WO 90/15070 and 92/10092, and Fodor et al., Science, 251, 767–77 (1991). U.S. Pat. No. 5,800,992, describes methods for making arrays of nucleic acid probes that can be used to detect the presence of a nucleic acid containing a specific nucleotide sequence. Methods of forming high density arrays of nucleic acids, peptides and other polymer sequences with a minimal number of synthetic steps are known. The nucleic acid array can be synthesized on a solid substrate by a variety of methods, including, but not limited to, light-directed chemical coupling, and mechanically directed coupling. Some techniques for making arrays include the U.S. Pat. Nos.: 5,143,854, 5,242,979, 5,252,743, 5,324,663, 5,384,261, 5,405,783, 5,412,087, 5,424,186, 5,445,934, 5,451,683, 5,482,867, 5,489,678, 5,491,074, 5,510,270, 5,527,681, 5,550,215, 5,571,639, 5,593,839, 5,599,695, 5,624,711, 5,631,734, 5,677,195, 5,744,101, 5,744,305, 5,753,788, 5,770,456, 5,831,070, and 5,856,011. See also, U.S. Ser. No. 09/079,324, U.S. Pat. No. 6,269,846, and PCT Application WO US99/00730.

In a preferred detection method, the array of immobilized nucleic acids, or probes, is contacted with a sample containing target nucleic acids, to which a flourescent label is attached. Target nucleic acids hybridize to the probes on the array and any non-hybridized nucleic acids are removed. The array containing the hybridized target nucleic acids are exposed to light which excites the flourescent label. The resulting flourescent intensity, or brightness, is detected.

Because nucleic acid sequences hybridize to other sequences which are their complement, once the sequence of a gene is known, probes can be designed to specifically target that gene. Methods of sequencing genes are well known to those of skill in the art. See, for example, Sambrook et al., for methods of sequencing DNA. The nucleic acid sequences of this invention may be used as probes for the genes to which their sequences are complementary. These probes may then be used alone or in combination for a wide variety of gene expression analyses.

Many biological functions are carried out by regulating the expression levels of various genes, either through changes in levels of transcription (e.g. through control of initiation, provision of RNA precursors, RNA processing, etc.) of particular genes, through changes in the copy number of the genetic DNA, or through changes in protein synthesis. For example, control of the cell cycle and cell differentiation, as well as diseases, are characterized by the variations in the transcription levels of a group of genes.

Gene expression is not only responsible for physiological functions, but also associated with pathogenesis. For example, the lack of sufficient functional tumor suppressor genes and/or the over expression of oncogene/protooncogenes leads to tumorgenesis. (See, e.g., Marshall, Cell, 64: 313–326 (1991) and Weinberg, Science, 254: 1138–1146 (1991.)) Thus, changes in the expression levels of particular genes (e.g. oncogenes or tumor suppressors), serve as signposts for the presence and progression of various diseases. Similarly, the effects of various treatment programs for a disease can be monitored through the analysis of the expression levels of genes associated with that disease.

For example, where the effects of a drug on gene expression are to be determined, the drug will be administered to an organism, a tissue sample, or a cell, and the gene expression levels will be analyzed. For example, nucleic acids are isolated from the treated tissue sample, cell, or a biological sample from the organism and from an untreated organism tissue sample or cell, hybridized to a high density probe array containing probes directed to the gene of interest and the expression levels of that gene are determined. The types of drugs that may be used in these types of experiments include, but are not limited to, antibiotics, antivirals, narcotics, anti-cancer drugs, tumor suppressing drugs, and any chemical composition which may affect the expression of genes in vivo or in vitro. The current invention is particularly suited to be used in the types of analyses described by, for example, pending U.S. Pat. No. 6,309,822 and PCT Application No. 98/11223, each of which is incorporated by reference in its entirety for all purposes. As described in Wodicka et al., Nature Biotechnology 15 (1997), (hereby incorporated by reference in its entirety for all purposes), because mRNA hybridization correlates to gene expression level, hybridization patterns can be compared to determine differential gene expression. As non-limiting examples: hybridization patterns from samples treated with certain types of drugs may be compared to hybridization patterns from samples which have not been treated or which have been treated with a different drug; hybridization patterns for samples infected with a specific virus may be compared against hybridization patterns from non-infected samples; hybridization patterns for samples with cancer may be compared against hybridization patterns for samples without cancer; hybridization patterns of samples from cancerous cells which have been treated with a tumor suppressing drug may be compared against untreated cancerous cells, etc. Zhang et al., Science 276 1268–1272, (hereby incorporated by reference in its entirety for all purposes), provides an example of how gene expression data can provide a great deal of insight into cancer research.

In one embodiment, the nucleic acid sequences of the current invention can be used for parallel analysis of gene expression under selective conditions. Without wishing to be limited, genetic selection under selective conditions could include: variation in the temperature of the organism's environment; variation in pH levels in the organism's environment; variation in an organism's food (type, texture, amount etc.); variation in an organism's surroundings; etc. Arrays, such as those in the present invention, can be used to determine whether gene expression is altered when an organism is exposed to selective conditions.

Methods for using nucleic acid arrays to analyze genetic selections under selective conditions are known. (See for example, R. Cho et al., Proc. Natl. Acad. Sci. 95 3752–3757 (1998) incorporated herein in its entirety for all purposes.) Cho et al. describes the use of a high-density array containing oligonucleotides complementary to every gene in the yeast *Saccharomyces cerevisiae* to perform two-hybrid protein-protein interaction screens for *S. cerevisiae* genes implicated in mRNA splicing and microtubule assembly. Cho et al. was able to characterize the results of a screen in a single experiment by hybridization of labeled DNA derived from positive clones. Briefly, as described by Cho et al., two proteins are expressed in yeast as fusions to either the DNA-binding domain or the activation domain of a transcription factor. Physical interaction of the two proteins reconstitutes transcriptional activity, turning on a gene essential for survival under selective conditions. In screening for novel protein-protein interactions, yeast cells are first transformed with a plasmid encoding a specific DNA-binding fusion protein. A plasmid library of activation domain fusions derived from genomic DNA is then introduced into these cells. Transcriptional activation fusions found in cells that survive selective conditions are considered to encode peptide domains that may interact with the DNA-binding domain fusion protein. Clones are then isolated from the two-hybrid screen and mixed into a single pool. Plasmid DNA is purified from the pooled clones and the gene inserts are amplified using PCR. The DNA products are then hybridized to yeast whole genome arrays for characterization. The methods employed by Cho et al. are applicable to the analysis of a range of genetic selections.

In another embodiment, the invention may be used in conjunction with the techniques which link specific proteins to the mRNA which encodes the protein. (See for example Roberts and Szostak Proc. Natl, Acad. Sci. 94 12297–12302 (1997) which is incorporated herein in its entirety for all purposes.) Hybridization of these mRNA-protein fusion compounds to arrays comprising 1 or more, 10 or more, $10^3$ or more, $10^6$ or more, $10^{12}$ or more nucleic acid probes provides a powerful tool for monitoring expression levels.

However, the utility of the nucleic acid sequences of this invention is not limited to gene expression analysis, in another embodiment, nucleic acid sequences of the current invention can be used to identify biallelic markers, providing a novel and efficient approach to the study of genetic variation. For example, methods for using high density arrays comprised of probes which are complementary to the genomic DNA of a particular species to interrogate polymorphisms are well known. (See for example, U.S. patent application Ser. No. 08/965,620 and U.S. Pat. No. 6,300,063 which are hereby incorporated herein for all purposes.)

In a further embodiment of the invention, genetic variation can be used to produce genetic maps of various strains of species. Winzeler et al., "Direct Allelic Variation Scanning of the Yeast Genome" Science 281:1194–1197 (1998), which is hereby incorporated for all purposes describe methods for conducting this type of screening with arrays containing probes complementary to the yeast genome. Briefly, genomic DNA from strains which are phenotypically different are isolated, fragmented, and labeled. Each strain is then hybridized to identical arrays comprised of the nucleic acid sequences complementary to the system being studied. Comparison of hybridization patterns between the various strains then serve as genetic markers. As described by Winzler et al, these markers can then be used for linkage analysis. High density arrays comprising 1 or more, 10 or more, $10^3$ or more, $10^6$ or more, or $10^{12}$ or more of the sequences disclosed in this invention can be used to study genetic variation using the methods described by Winzler et al.

In another embodiment, the present invention may be used for cross-species comparisons. One skilled in the art will appreciate that it is often useful to determine whether a gene present in one species (the interrogation species), for example the rat, is present in a conserved format in another species (the queried species), including, without limitation, mouse, human, chicken, zebrafish, drosophila, or yeast. See, for example, Andersson et al., Mamm Genome 7(10):717–734 (1996) which is hereby incorporated by reference for all purposes, which describes the utility of cross-species comparisons. The use of arrays comprising 1 or more, 10 or more, $10^3$ or more, $10^6$ or more, $10^{12}$ or more of the nucleic acid sequences disclosed in this invention can be used to determine whether any of the sequence from one or more of the interrogation species genes is conserved in another species by, for example, hybridizing genomic nucleic acid samples from a species to be queried to an array comprised of the sequences from the interrogation species, or vice versa. Areas of hybridization will yield genomic regions where the nucleotide sequence is highly conserved between the interrogation species and the queried species.

In another embodiment, the present invention may be used to characterize the genotype of knockouts. Methods for using gene knockouts to identify a gene are well known. See for example, Lodish et al. *Molecular Cell Biology, 3$^{rd}$ Edition,* Scientific American Books pub pp. 292–296 and U.S. Pat. No. 5,679,523 which are hereby incorporated by reference for all purposes. By isolating genomic nucleic acid samples from knockout species with a known phenotype and hybridizing the samples to an array comprising 1 or more, 10 or more, $10^3$ or more, $10^6$ or more, or $10^{12}$ or more of the sequences disclosed in this invention, candidates genes which contribute to the phenotype will be identified and made accessible for further characterization.

In another embodiment, the present invention may be used to identify new gene family members. Methods of screening libraries with probes are well known. (See, for example, Sambrook et al, incorporated by reference above.) Because the present invention is comprised of nucleic acid sequences from specific known genes, 1 or more, 10 or more, $10^3$ or more, $10^6$ or more, or $10^{12}$ or more of sequences disclosed in this invention may be used as probes to screen genomic libraries to look for additional family members of those genes from which the target sequences are derived.

In another embodiment of the invention, the sequences of this invention may be used to generate primers directed to their corresponding genes as disclosed in the Genbank or any other public database. These primers may be used in such basic techniques as sequencing or PCR, see for example Sambrook et al., incorporated by reference above.

In another embodiment, the invention provides a pool of nucleic acid sequences to be used as ligands for specific genes. The sequences disclosed in this invention may be used as ligands to their corresponding genes as disclosed in the Genbank or any other public database. Compounds which specifically bind known genes are of interest for a variety of uses. One particular clinical use is to act as an antisense protein which specifically binds and disables a gene which has been, for example, linked to a disease. Methods and uses for ligands to specific genes are known. See for example, U.S. Pat. No. 5,723,594 which is hereby incorporated by reference in its entirety for all purposes.

Not all the applications for the sequences of this invention rely on the correlation of the nucleic acid sequence to a gene. In one embodiment, the present invention may be used to provide nucleic acid sequences to be used as tag sequences. Tag sequences are a type of genetic "bar code" which can be used to label compounds of interest. See for example, U.S. patent application Ser. No. 08/626,285, U.S. Provisional Patent Application No. 60/140,359 and European Patent Application No. EP97302313.8 each of which is hereby incorporated by reference in its entirety for all purposes.

Hybridization of pools of tag sequences to a solid support to form "tag arrays" is described in the references above. These references also describe various uses for tag arrays.

The analysis of deletion mutants using tag sequences is described in, for example, Shoemaker et al., Nature Genetics 14 450–456 (1996), which is hereby incorporated by reference in its entirety for all purposes. Shoemaker et al. describes the use of PCR to generate large numbers of deletion strains. Each deletion strain is labeled with a unique 20-base tag sequence that can be hybridized to a high-density oligonucleotide array. The tags serve as unique identifiers (molecular bar codes) that allow analysis of large numbers of deletion strains simultaneously through selective growth conditions. The use of tag sequences in solution or hybridized to a solid support need not be limited to this example however. The utility of using unique known short oligonucleotide sequences label various compounds will be apparent to one skilled in the art.

Most of the embodiments described thus far have incorporated the use of directed arrays, that is arrays designed to perform a specific type of interrogation, for example, the comparison of expression patterns generated by the hybridization of samples derived from a specific species. However, the tag array described above is an example of a generic array which can be used for a wide variety of applications.

A powerful form of the generic array is the n-mer array. N-mer arrays comprise a solid support to which are attached all possible nucleic acid sequences of a give length. Therefore, a 2-mer array comprises all possible oligonucleotides containing 2 base positions. Because each position can be filled with one of four possible bases, adenine (A), cytosine (C), thymine (with uracil replacing thymine in RNA) (T(U)), and guanine (G), an n-mer array comprising all possible n-mers contains $4^n$ different oligonucleotide probes. Thus, a 2-mer array comprises $4^2$ or 16 different oligonucleotide sequences. A 10-mer array comprises $4^{10}$ or 1,048,576 distinct sequences and a 25-mer array comprises $4^{25}$ or over $1 \times 10^{15}$ different oligonucleotide sequences. By way of explanation, all possible oligonucleotide 25-mers may be depicted in the fashion:

N1-N2-N3-N4-N5-N6-N7-N8-N9-N10-N11-N12-N13-N14-N15-N16-N17-N18-N19-N20-N21-N22-N23-N24-N25 where each N is selected from the group comprising A, C, T(U), G and analogs thereof.

U.S. Pat. No. 5,800,992 describes a wide number of applications for n-mer arrays. N-mer arrays allow for the use of the same array design to accommodate a variety of different analyses. For example, variant detection, expression analysis and fingerprinting and methods of mapping are all described in the '992 patent using n-mer arrays.

Methods of detecting mutations by ligation to complete n-mer DNA arrays are described in U.S. patent application Ser. No. 09/394,230. The '230 application provides methods to determine the presence of mutations in a target polynucleotide using complete or substantially complete n-mer arrays of polynucleotide probes having double-stranded polynucleotide regions with variable single-stranded regions known as "n-mer overhangs." One method comprises hybridizing fragments of a target polynucleotide with the polynucleotide probes of the array. The polynucleotide probes of another identical or substantially identical array are similarly hybridized with fragments of a reference polynucleotide. The patterns of hybridization of the target and reference polynucleotides on the arrays can be directly compared, allowing the determination of the presence of mutations.

The '230 application further discloses that the sensitivity and accuracy of the methodology can be increased by generating virtual tilings from the hybridization patterns and comparing the virtual tilings directly. (See, for example, U.S. Pat. No. 5,837,832 which is hereby incorporated by reference in its entirety for all purposes.) Such direct comparison subtracts out potentially confusing signals resulting from systematic and reproducible cross-hybridization and multiple probe-target interactions. The methods afforded greater than 90% mutation detection sensitivity in 2.5 kbp targets (on 8-mer arrays), with extremely high accuracy (i.e., low number of false positives, <0.02% per base). The virtual tiling step permits focused search for the detection of unanticipated mutations (insertions, deletions, multiple point mutations) within a target by electronically assembling the appropriate query probes.

The methods described in the '230 application involve not only the determination of the presence of a mutation but also the identification of the location and type of the mutation, i.e., whether the mutation is a single or multiple base substitution, deletion or insertion. The methods can also be used to detect both homozygous and heterozygous mutations as well as polymorphisms. Further, the methods can be used to compare two or more unknown polynucleotide sequences to determine if they are identical, without necessarily having to know the sequence of one of the polynucleotides to act as a reference. These methods permit such analyses because, unlike the traditional techniques which compare sequences, these methods compare hybridization patterns.

Thus, multiple polynucleotides can be rapidly and accurately compared to determine if they are identical in sequence. These rapid and accurate methods are particularly useful for forensic purposes to compare polynucleotides from a variety of sources without necessarily sequencing or having to know the sequence of any of the polynucleotides. These methods may offer advantages over the conventional methods in terms of their accuracy, sensitivity, and thus can be expected to gain wide-spread acceptance in a courtroom. Further, the methods can be used to screen quickly the mutational effects of drugs, chemicals, radiation, stress or environmental factors on genes, by comparing the hybridization patterns before and after exposure. The versatility of the methods can be further exploited by using parallel processing techniques described below and in the U.S. Pat. No. 5,545,531, whereby multiple polynucleotide sequences can be analyzed simultaneously.

In a preferred embodiment, the hybridized nucleic acids are detected by detecting one or more labels attached to the sample nucleic acids. The labels may be incorporated by any of a number of means well known to those of skill in the art. In one embodiment, the label is simultaneously incorporated during the amplification step in the preparation of the sample nucleic acids. Thus, for example, polymerase chain reaction (PCR) with labeled primers or labeled nucleotides will provide a labeled amplification product. In another embodiment, transcription amplification, as described above, using a labeled nucleotide (e.g. fluorescein-labeled UTP and/or CTP) incorporates a label into the transcribed nucleic acids.

Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3H$, $^{125}I$, $^{35}S$, $^{14}C$, or $^{32}P$), phosphorescent labels, enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241, each of which is hereby incorporated by reference in its entirety for all purposes.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

The label may be added to the target nucleic acid(s) prior to, or after the hybridization. So called "direct labels" are detectable labels that are directly attached to or incorporated into the target nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an aviden-conjugated fluorophore will bind the biotin bearing hybrid duplexes providing a label that is easily detected. For a detailed review of methods of labeling nucleic acids and detecting labeled hybridized nucleic acids see *Laboratory Techniques in Biochemistry and Molecular Biology,* Vol 24: *Hybridization With Nucleic Acid Probes,* P. Tijssen, ed. Elsevier, N.Y., (1993) which is hereby incorporated by reference in its entirety for all purposes.

Fluorescent labels are preferred and easily added during an in vitro transcription reaction. In a preferred embodiment, fluorescein labeled UTP and CTP are incorporated into the RNA produced in an in vitro transcription reaction as described above.

In a preferred embodiment, a computer system is used to analyze the hybridization of target sequences to the array. The computer system can be designed to look at hybridization only to probes which are of interest for the particular experiment being performed. For example, if the array is being used to evaluate the expression of a particular gene or genes, the computer system can be designed to look only at the hybridization pattern of the target sequence to those sequences on the array which are complementary to the gene or genes of interest. Similar types of analyses may be performed for arrays designed to conduct other types of experiments such as variant detection. U.S. Provisional Patent Applications Nos. 60/184,704, filed on Feb. 24, 2000 and 60/182,288, describe algorithms which can be used to obtain target sequence data from hybridization to arrays where probe placement is based on factors unrelated to target sequence (i.e. edge minimization techniques).

EXAMPLE

The following examples describe in detail the synthesis of the array, fragmentation of target and reference polynucleotides, hybridization and ligation, washing and staining of arrays, and data analysis. While these examples further clarify the methods described herein, they are not to be construed as limiting the scope of the invention.

Example 1

Expression Monitoring by Hybridization to High Density Oligonucleotide Arrays

The following example serves to illustrate the type of experiment that could be conducted using the invention.

Arrays containing the desired number of probes can be synthesized using the method described in U.S. Pat. No. 5,143,854, incorporated by reference above. Extracted poly (A)$^+$RNA can then be coverted to cDNA using the methods described below. The cDNA is then transcribed in the presence of labeled ribonucleotide triphosphates. The label may be biotin or a dye such as fluorescein. RNA is then fragmented with heat in the presence of magnesium ions. Hybridizations are carried out in a flow cell that contains the two-dimensional DNA probe arrays. Following a brief washing step to remove unhybridized RNA, the arrays are scanned using a scanning confocal microscope.

1. A Method of RNA Preparation

Labeled RNA is prepared from clones containing a T7 RNA polymerase promoter site by incorporating labeled ribonucleotides in an IVT reaction. Either biotin-labeled or fluorescein-labeled UTP and CTP (1:3 labeled to unlabeled) plus unlabeled ATP and GTP is used for the reaction with 2500 U of T7 RNA polymerase. Following the reaction unincorporated nucleotide triphosphates are removed using size-selective membrane such as Microcon—100, (Amicon, Beverly, Mass.). The total molar concentration of RNA is based on a measurement of the absorbance at 260 nm. Following quantitation of RNA amounts, RNA is fragmented randomly to an average length of approximately 50 bases by heating at 94° in 40 mM Tris-acetate pH 8.1, 100 mM potassium acetate, 30 mM magnesium acetate, for 30 to 40 mm. Fragmentation reduces possible interference from RNA secondary structure, and minimizes the effects of multiple interactions with closely spaced probe molecules. For material made directly from cellular RNA, cytoplasmic RNA is extracted from cells by the method of Favaloro et al. Methods Enzymol. 65:718–749 (1980) hereby incorporated by reference for all purposes, and poly (A)$^+$ RNA is isolated with an oligo dT selection step using, for example, Poly (A) tract, (Promega, Madison, Wis.). RNA can be amplified using a modification of the procedure described by Eberwine et al. Proc. Natl. Acad. Sci. USA 89:3010–3014 (1992) hereby incorporated by reference for all purposes. Microgram amounts of poly (A)$^+$ RNA are converted into double stranded cDNA using a cDNA synthesis kit (kits may be obtained from Life Technologies, Gaithersburg, Md.) with an oligo dT primer incorporating a T7 RNA polymerase promoter site. After second-strand synthesis, the reaction mixture is extracted with phenol/chloroform, and the double-stranded DNA isolated using a membrane filtration step using, for example, Microcon—100, (Amicon). Labeled cRNA can be made directly from the cDNA pool with an JVT step as described above. The total molar concentration of labeled cRNA is determined from the absorbance at 260 nm and assuming an average RNA size of 1000 ribonucleotides. The commonly used convention is that 1 OD is equivalent to 40 ug of RNA, and that 1 ug of cellular mRNA consists of 3 pmol of RNA molecules. Cellular rnRNA may also be labeled directly without any intermediate cDNA synthesis steps. In this case, Poly (A)$^+$ RNA is fragmented as described, and the 5' ends of the fragments are kinased and then incubated overnight with a biotinylated oligoribonucleotide (5'-biotin-AAAAAA-3') in the presence of T4 RNA ligase (available from Epicentre Technologies, Madison, Wis. ). Alternatively, mRNA has been labeled directly by UV-induced cross-linking to a psoralen derivative linked to biotin (available from Schleicher & Schuell, Keene, N.H.).

2. Array hybridization and Scanning

Array hybridization solutions can be made containing 0.9 M NaCl, 60 mM EDTA, and 0.005% Triton X-100, adjusted to pH 7.6 (referred to as 6×SSPE-T). In addition, the solutions should contain 0.5 mg/ml unlabeled, degraded herring sperm DNA (available from Sigma, St. Louis, Mo.). Prior to hybridization, RNA samples are heated in the hybridization solution to 99° C. for 10 min, placed on ice for 5 mm, and allowed to equilibrate at room temperature before being placed in the hybridization flow cell. Following hybridization, the solutions are removed, the arrays washed with 6×SSPE-T at 22° C. for 7 mm, and then washed with 0.5×SSPE-T at 40° C. for 15 min. When biotin labeled RNA is used the hybridized RNA should be stained with a streptavidinphycoerythrin in 6×SSPE-T at 40° C. for 5 min. The arrays are read using a scanning confocal microscope made by Molecular Dynamics (commercially available through Affymetrix, Santa Clara, Calif.). The scanner uses an argon ion laser as the excitation source, with the emission detected by a photomultiplier tube through either a 530 nm bandpass filter (flourescein) or a 560 nm longpass filter (phycoerythrin). Nucleic acids of either sense or antisense orientations may be used in hybridization experiments. Arrays for probes with either orientation (reverse complements of each other) are made using the same set of photolithgraphic masks by reversing the order of the photochemical steps and incorporating the complementary nucleotide.

3. Quantitative Analysis of Hybridization Patterns and Intensities

Following a quantitative scan of an array, a grid is aligned to the image using the known dimensions of the array and the corner control regions as markers. The image is then reduced to a simple text file containing position and intensity information using software developed at Affymetrix (available with the confocal scanner). This information is merged with another text file that contains information relating physical position on the array to probe sequence and the identity of the RNA (and the specific part of the RNA) for which the oligonucleotide probe is designed. The quantitative analysis of the hybridization results involves a simple form of pattern recognition based on the assumption that, in the presence of a specific RNA, the perfect match (PM) probes will hybridize more strongly on average than their mismatch (MM) partners. The number of instances in which the PM hybridization is larger than the MM signal is computed along with the average of the logarithm of the PM/MM ratios for each probe set. These values are used to make a decision (using a predefined decision matrix) concerning the presence or absence of an RNA. To determine the quantitative RNA abundance, the average of the difference (PM−MM) for each probe family is calculated. The advantage of the difference method is that signals from random cross-hybridization contribute equally, on average, to the PM and MM probes, while specific hybridization contributes more to the PM probes. By averaging the pairwise differences, the real signals add constructively while the contributions from cross-hybridization tend to cancel. When assessing the differences between two different RNA samples, the hybridization signals from side-by-side experiments on identically synthesized arrays are compared directly. The magnitude of the changes in the average of the difference (PM−MM) values is interpreted by comparison with the results of spiking experiments as well as the signals observed for the internal standard bacterial and phase RNAs spiked into each sample at a known amount. Data analysis programs, such as those described in U.S. Ser. No. 08/828,952 perform these operations automatically.

Example 2

Sample Analysis Using a 10-mer Array

FIGS. 2–5 show the hybridization pattern resulting from the hybridization of a sample of DNA to an array containing all possible 10-mers. The array was manufactured using photolithography techniques. Photolithography techniques are described in, for example, U.S. Pat. Nos. 5,143,854; and 5,489,678, which are incorporated herein by reference. According to the techniques disclosed in these patents, the oligonucleotides are synthesized stepwise on a substrate at positionally separate and defined positions. Use of photosensitive blocking reagents allows for defined sequences of synthetic steps over the surface of a matrix pattern. By use of the binary masking strategy, the surface of the substrate can be positioned to generate a desired pattern of regions, each having a defined sequence oligonucleotide synthesized and immobilized thereto.

In the most preferred embodiment, the regions containing individual probes (also called features, known locations, or pixels) may be very small, usually less than about 100 $\mu m \times 100$ $\mu m$, more usually less than about 50 $\mu m \times 50$ $\mu m$. The array shown in FIGS. 2–5 contained 25 micron features. Current photolithography technology allows features of less than about 10 $\mu m \times 10$ $\mu m$, about 3 $\mu m \times 3$ $\mu m$, or less. U.S. Pat. Nos. 5,658,734 and 6,083,697 disclose photo-resist-based processes which can give a resolution of 1 $\mu m \times 1$ $\mu m$ or smaller.

Figure 2:
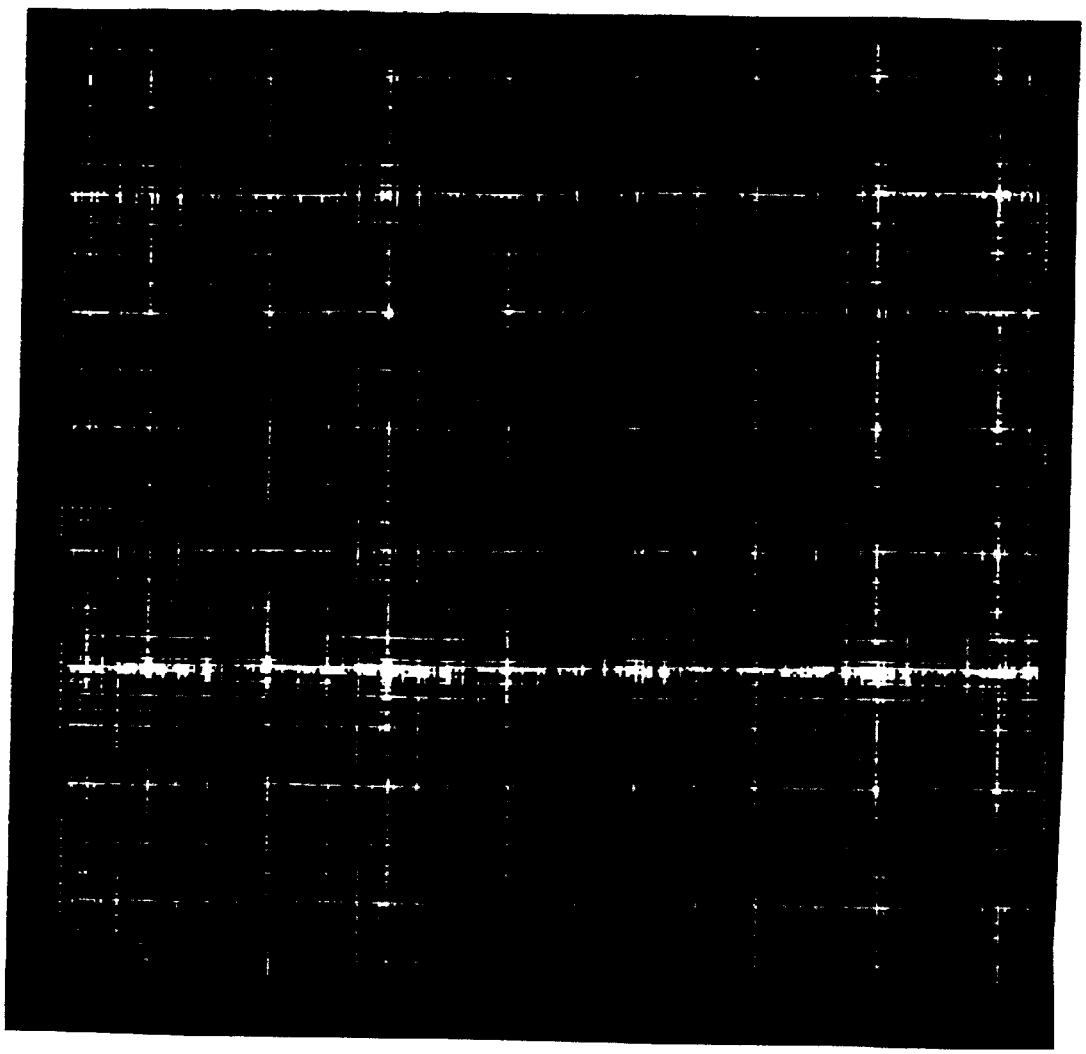
FIG. 2 depicts the hybridization pattern of a nucleic acid sample hybridized to the A chip of a 10-mer array.
Figure 3:
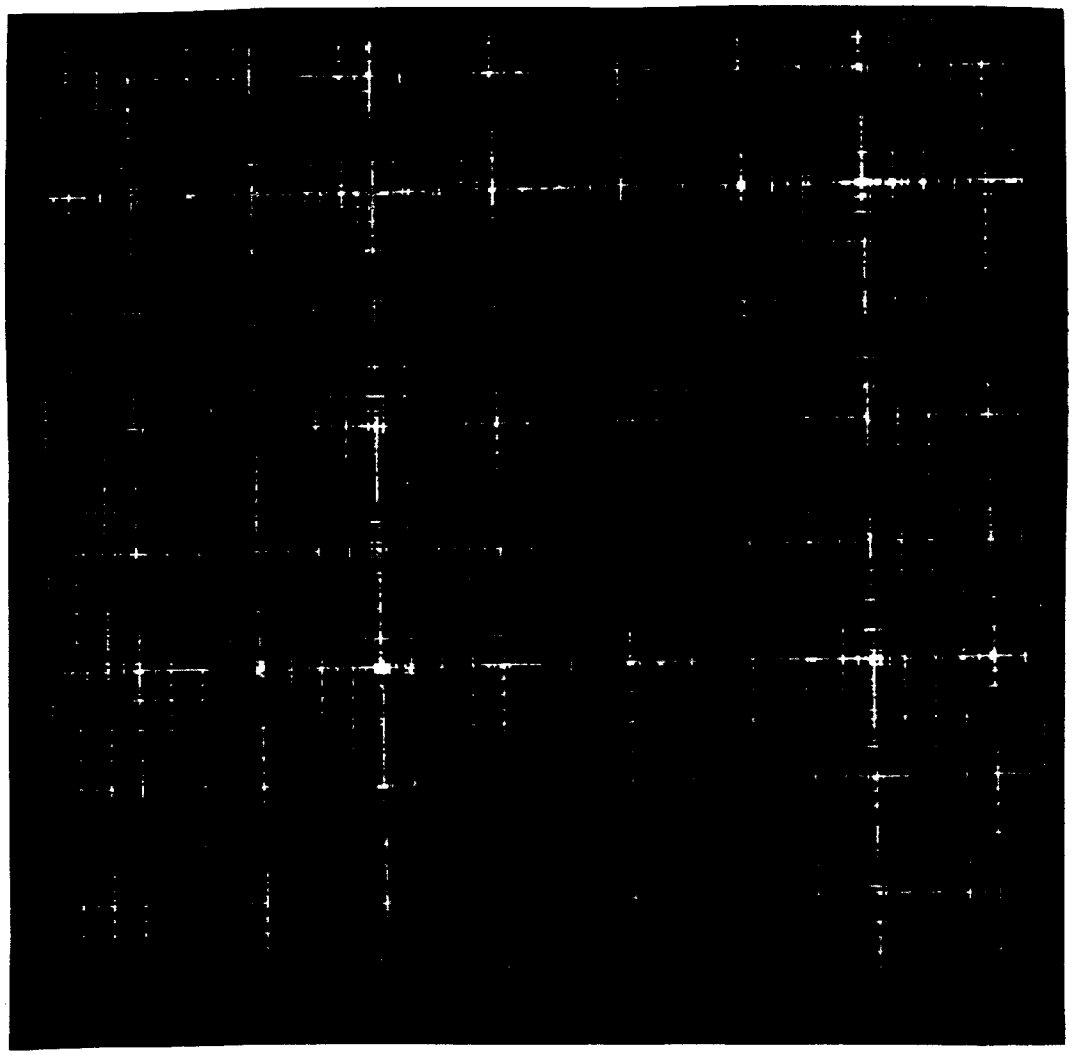
FIG. 3 depicts the hybridization pattern of a nucleic acid sample hybridized to the B chip of a 10-mer array.
Figure 4:
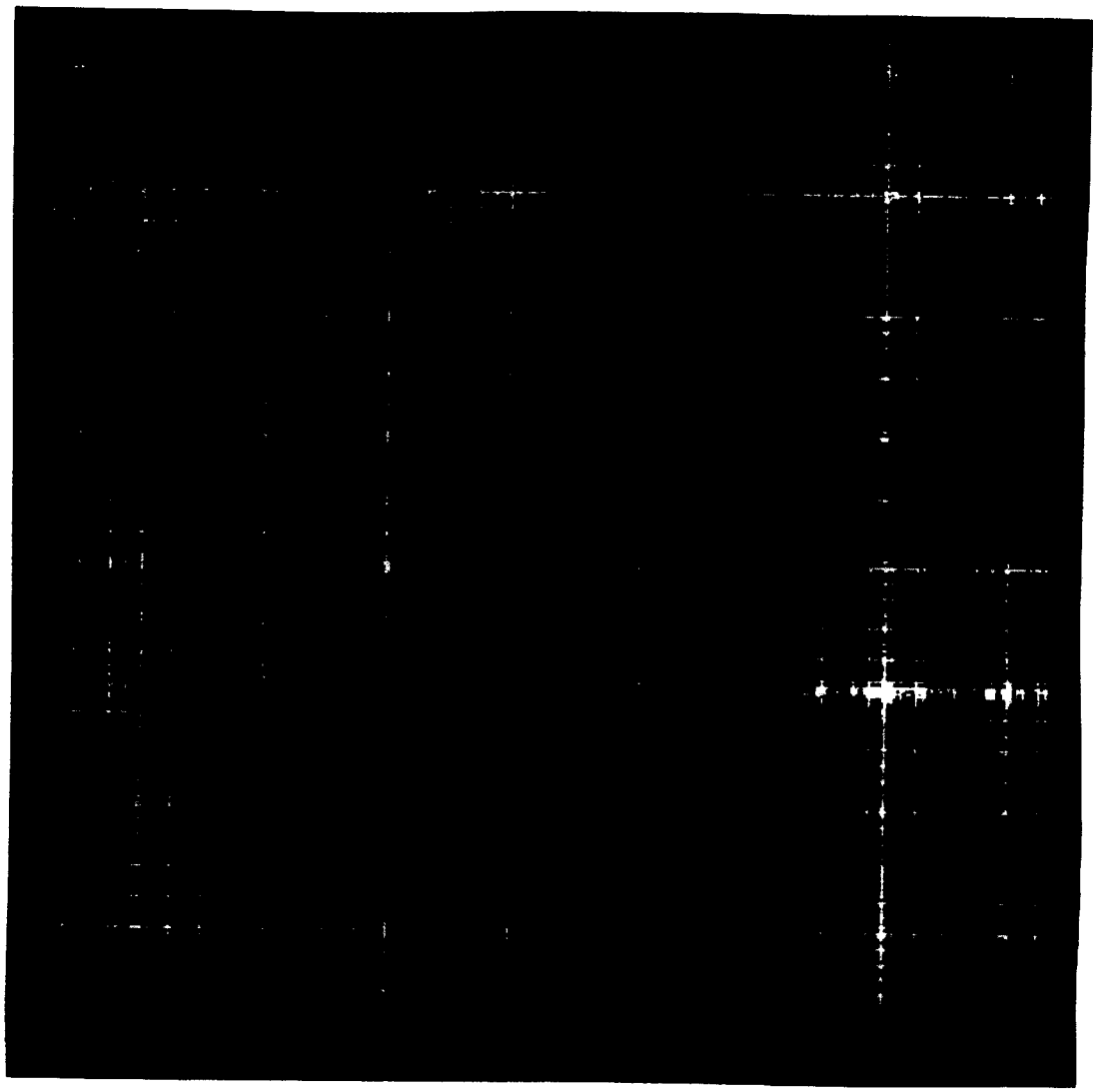
FIG. 4 depicts the hybridization pattern of a nucleic acid sample hybridized to the C chip of a 10-mer array.
Figure 5:
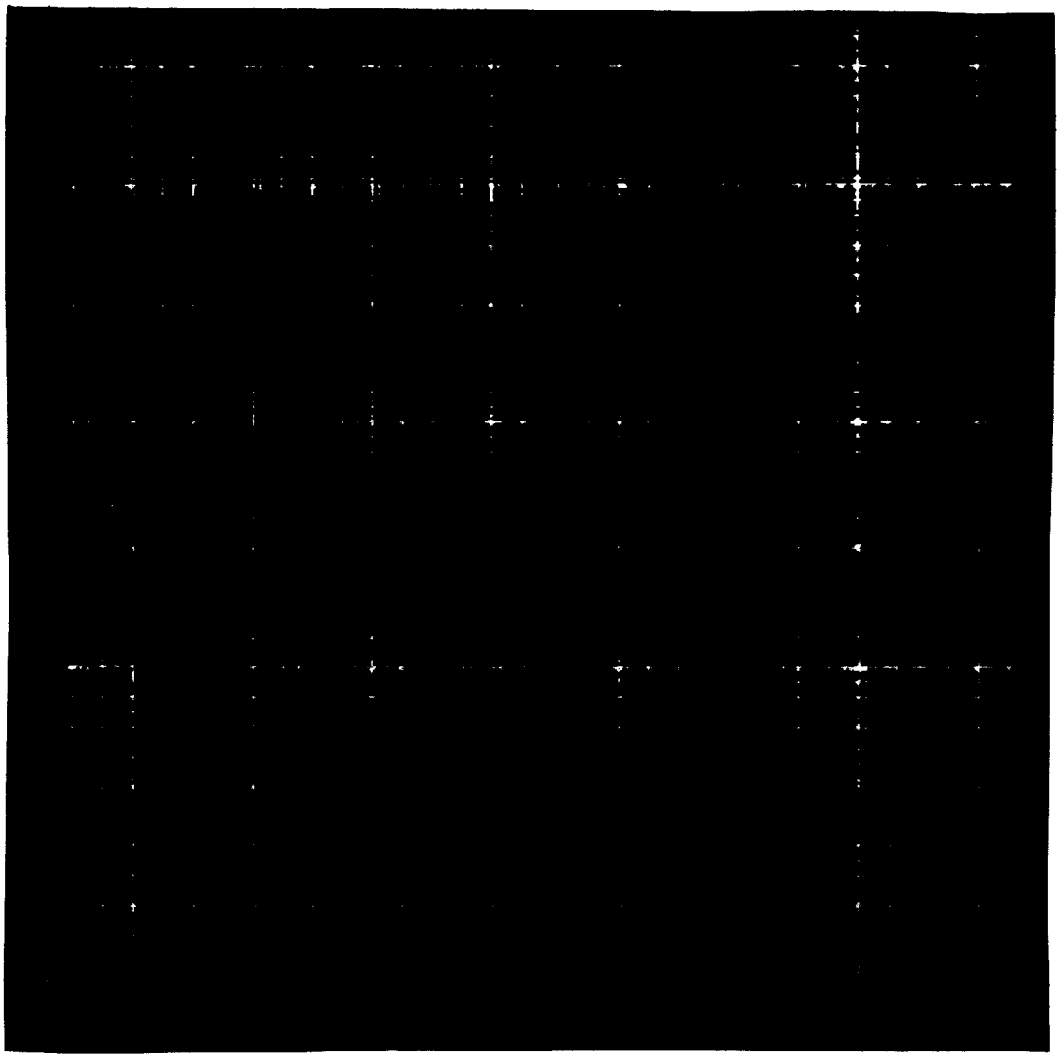
FIG. 5 depicts the hybridization pattern of a nucleic acid sample hybridized to the D chip of a 10-mer array.

At a feature size of 10 $\mu m^2$, all possible 10mers could fit on a single substrate the size of a dime. At a size of 1 $\mu m \times 1$ $\mu m$, all possible 20 mers would fit on 100 10 $cm^2$ substrates. Thus the present technology provides for making a single substrate of that size having all one million, seven million or more oligonucleotides, depending on the feature size and the size of the substrate. When the number of desired oligonucleotides is so large that a single substrate is impractical, multiple substrates may be used. See for example, U.S. Pat. No. 5,874,219 for methods of making arrays of arrays. The 10-mer array of FIGS. 2–5 was manufactured on a single 3" square wafer and then divided into four different chips for hybridization and scanning. Each chip is then given the name of A,B,C or D respectively. FIG. 2 depicts the hybridization pattern of a nucleic acid sample hybridized to the A chip. FIG. 3 depicts the hybridization pattern of a nucleic acid sample hybridized to the B chip. FIG. 4 depicts the hybridization pattern of a nucleic acid sample hybridized to the C chip. FIG. 5 depicts the hybridization pattern of a nucleic acid sample hybridized to the D chip.

Although the pattern of the features which contain specific sequences is theoretically not important, for practical reasons certain patterns will be preferred in synthesizing the oligonucleotides. The application of binary masking algorithms for generating the pattern of known oligonucleotide probes is described in U.S. Pat. No. 5,489,678 which is hereby incorporated by reference in its entirety for all purposes. By use of these binary masks, a highly efficient means is provided for producing the substrate with the desired matrix pattern of different sequences. Although the binary masking strategy allows for the synthesis of all lengths of polymers, the strategy may be easily modified to provide only polymers of a given length. This is achieved by omitting steps where a subunit is not attached.

The strategy for generating a specific pattern may take any of a number of different approaches. These approaches are well described the '678 patent, and include a number of binary masking approaches which will not be exhaustively discussed herein. However, the binary masking and binary synthesis approaches provide a maximum of diversity with a minimum number of actual synthetic steps.

Although, not described in detail here, light directed synthesis technology would typically use a photosensitive protective group on an oligonucleotide. In particular, the photoprotective group on the nucleotide molecules may be selected from a wide variety of positive light reactive groups preferably including nitro aromatic compounds such as o-nitro-benzyl derivatives or benzylsulfonyl. See, e.g., Gait (1984) *Oligonucleotide Synthesis: A Practical Approach*, IRL Press, Oxford, which is hereby incorporated herein by reference. In a preferred embodiment, 6-nitro-veratryl oxycarbony (NVOC), 2-nitrobenzyl oxycarbonyl (NBOC), or α,α-dimethyl-dimethoxybenzyl oxycarbonyl (DEZ) is used. Photoremovable protective groups are described in, e.g., Patchornik (1970) *J. Amer. Chem. Soc.* 92:6333–6335; and Amit et al. (1974) *J. Organic Chem.* 39:192–196; each of which is hereby incorporated herein by reference. Further details are described in U.S. Pat. No. 5,800,992.

Various types of linkers may be used to attach the oligonucleotide to a silicon substrate. The 10-mer array depicted in FIGS. 2–5 utilized a MenPOC linker. A more detailed description is provided in U.S. Pat. Nos. 5,889,165, 5,744,101, 5,599,695, 5,424,186, 5,510,270, 5,744,305 and 5,831,070 each of which is incorporated by reference in its entirety for all purposes. A photosensitive blocked nucleotide may be attached to specific locations of unblocked prior cycles of attachments on the substrate and can be successively built up to the correct length oligonucleotide probe. The 10-mer array depicted in FIGS. 2–5 was built using 40 cycles, each cycle requiring the steps of masking, exposure and synthesis.

As in the above example, multiple substrates may be simultaneously exposed to a single target sequence where each substrate is a duplicate of one another or where, in combination, multiple substrates together provide the complete or desired subset of possible subsequences. This provides the opportunity to overcome a limitation of the density of positions on a single substrate by using multiple substrates. See for example, U.S. Pat. Nos. 5,874,219 and 5,545,131 each of which is incorporated by reference in its entirety for all purposes. In the extreme case, each probe might be attached to a single bead or substrate and the beads sorted by whether there is a binding interaction. Those beads which do bind might be encoded to indicate the subsequence specificity of reagents attached thereto.

Then, the target may be bound to the whole collection of beads and those beads that have appropriate specific reagents on them will bind to the target. Then a sorting system may be utilized to sort those beads that actually bind the target from those that do not. This may be accomplished by presently available cell sorting devices or a similar apparatus. After the relatively small number of beads which have bound the target have been collected, the encoding scheme may be read off to determine the specificity of the reagent on the bead. An encoding system may include a magnetic system, a shape encoding system, a color encoding system, or a combination of any of these, or any other encoding system. Once again, with the collection of specific interactions that have occurred, the binding may be analyzed for sequence, fingerprint, mapping or other information.

Another method utilizes synthetic beads or fibers. This would use another substrate, such as a teflon copolymer graft bead or fiber, which is covalently coated with an organic layer (hydrophilic) terminating in hydroxyl sites (commercially available from Molecular Biosystems, Inc.) This would offer the same advantage as the Durapore.TM. membrane, allowing for immediate phosphate linkages, but would give additional contour by the 3-dimensional growth of oligomers.

The label used to detect the target sequences will be determined, in part, by the detection methods being applied. Thus, the labeling method and label used are selected in combination with the actual detecting systems being used. A quickly and easily detectable signal is preferred. The VLSIPS apparatus is designed to easily detect a fluorescent label, so fluorescent tagging of the target sequence is preferred. Other suitable labels include heavy metal labels, magnetic probes, chromogenic labels (e.g., phosphorescent labels, dyes, and fluorophores) spectroscopic labels, enzyme linked labels, radioactive labels, and labeled binding proteins. Additional labels are described in U.S. Pat. No. 4,366,241, which is incorporated herein by reference. See also U.S. Pat. No. 5,990,479 which discloses organo luminescent semiconductor nanocrystal compounds which are capable of linking to affinity molecules such as nucleic acids.

Once a particular label has been selected, appropriate labeling protocols will be applied, as described below for specific embodiments. Standard labeling protocols for nucleic acids are described, e.g., in Sambrook et al.; Kambara, H. et al. (1988) *BioTechnology* 6:816–821; Smith, L. et al. (1985) *Nuc. Acids Res.* 13:2399–2412; for polypeptides, see, e.g., Allen G. (1989) *Sequencing of Proteins and Peptides*, Elsevier, New York, especially chapter 5, and Greenstein and Winitz (1961) *Chemistry of the Amino Acids*, Wiley and Sons, New York. Carbohydrate labeling is described, e.g., in Chaplin and Kennedy (1986) *Carbohydate Analysis: A Practical Approach*, IRL Press, Oxford. Labeling of other polymers will be performed by methods applicable to them as recognized by a person having ordinary skill in manipulating the corresponding polymer. Other methods of labeling such as those described in PCT Patent No. PCT/FR/99/03193 and U.S. Provisional Patent Application No. 60/172,135 and U.S. patent application Ser. No. 09/737,761 may be employed.

In some embodiments, the target need not actually be labeled if a means for detecting where interaction takes place is available. These may involve, for example, using an intercalating dye which intercalates only into double stranded segments, e.g., where interaction occurs. See, e.g., Sheldon et al. U.S. Pat. No. 4,582,789.

The hybridization conditions between probe and target should be selected such that the specific recognition interaction, i.e., hybridization, of the two molecules is both sufficiently specific and sufficiently stable. See, e.g., Hames and Higgins (1985) *Nucleic Acid Hybridisation: A Practical Approach*, IRL Press, Oxford. These conditions will be dependent both on the specific sequence and often on the guanine and cytosine (GC) content of the complementary hybrid strands. The conditions may often be selected to be universally equally stable independent of the specific sequences involved. This typically will make use of a reagent such as an arylammonium buffer. See, Wood et al. (1985) "Base Composition-independent Hybridization in Tetramethylammonium Chloride: A Method for Oligonucleotide Screening of Highly Complex Gene Libraries," *Proc. Natl. Acad. Sci. USA,* 82:1585–1588; and Krupov et al. (1989) "An Oligonucleotide Hybridization Approach to DNA Sequencing," *FEBS Letters,* 256:118–122; each of which is hereby incorporated herein by reference.

The detection methods used to determine where hybridization has taken place will typically depend upon the label selected above. Thus, for a fluorescent label a fluorescent detection step will typically be used. U.S. Pat. Nos. 5,143,854 and 5,489,678 describe apparatus and mechanisms for scanning a substrate matrix using fluorescence detection, but a similar apparatus is adaptable for other optically detectable labels.

The detection method provides a positional localization of the region where hybridization has taken place. However, the position is correlated with the specific sequence of the probe since the probe has specifically been attached or synthesized at a defined substrate matrix position. Having collected all of the data indicating the subsequences present in the target sequence, this data may be aligned by overlap to reconstruct the entire sequence of the target, as illustrated above.

Data is typically analyzed using a computer system. See, for example, U.S. Pat. Nos. 5,733,729, 5,795,716, 5,974,164 and 5,981,956 each of which is incorporated by reference in its entirety for all purposes.

Conclusion

The above descriptions are illustrative and not restrictive. Many variations of the invention will become apparent to those of skill in the art upon review of this disclosure. Merely by way of example a variety of substrates, polymers, linking groups, synthesis initiation sites, and other materials may be used without departing from the scope of the invention. The scope of the invention should, therefore, be determined not with reference to the above description, but instead should be determined with reference to the appended claims along with their full scope of equivalents.

What is claimed is:

1. A nucleic acid array comprising at least 70% of all possible, different oligonucleotide sequences, wherein the different sequence lengths are 30 mers long, are on a solid support and are present at a density of at least 1,000 per $cm^2$.

2. A nucleic acid array in accordance with claim 1, comprising a substantially complete set of all possible, different oligonucleotide sequences, wherein the different sequence lengths are 30 mers long and are being present at a density of at least 1,000 per $cm^2$.

3. A nucleic acid array comprising at least 70% of $4^n$ unique oligonucleotide sequences of a given length n wherein n is 30 and wherein said array is formed on a substrate with a surface having an array of at least 1,000 distinct oligonucleotides in a surface area of 1 $cm^2$, each distinct oligonucleotide being disposed at a separate, defined position in said array.

4. A nucleic acid array in accordance with claim 3, comprising a substantially complete set of $4^n$ unique oligonucleotide sequences of a given length n wherein n is a number from 10 to 20.

5. A nucleic acid array in accordance with claim 3 comprising a complete set $4^n$ unique oligonucleotide sequences of a given length n wherein n is 10.

6. A method for nucleic acid hybridization between nucleic acid probes on a solid support and a nucleic acid target, comprising;
   isolating nucleic acids from an organism, tissue or cell;
   hybridizing the nucleic acids to the array of claim 5; and
   detecting a hybridization pattern created by the hybridization of the isolated nucleic acids and the nucleic acids on the array.

7. A nucleic acid array in accordance with claim 1 wherein the different sequence lengths are 20 mers long.

8. A nucleic acid array in accordance with claim 1 wherein the different sequence lengths are 12 mers long.

9. A nucleic acid array in accordance with claim 1 wherein the different sequence lengths are 10 mers long.

10. A nucleic acid array in accordance with claim 2 wherein the different sequence lengths are 20 mers long.

11. A nucleic acid array in accordance with claim 2 wherein the different sequence lengths are 12 mers long.

12. A nucleic acid array in accordance with claim 2 wherein the different sequence lengths are 10 mers long.

* * * * *